(12) United States Patent
Ganapathiappan et al.

(10) Patent No.: US 10,583,612 B2
(45) Date of Patent: Mar. 10, 2020

(54) THREE-DIMENSIONAL (3D) PRINTING METHOD

(71) Applicant: Hewlett-Packard Development Company, L.P., Houston, TX (US)

(72) Inventors: Sivapackia Ganapathiappan, Los Altos, CA (US); Howard S. Tom, San Jose, CA (US); Hou T. Ng, Campbell, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 818 days.

(21) Appl. No.: 15/100,584

(22) PCT Filed: Jan. 29, 2014

(86) PCT No.: PCT/US2014/013511
§ 371 (c)(1),
(2) Date: May 31, 2016

(87) PCT Pub. No.: WO2015/108543
PCT Pub. Date: Jul. 23, 2015

(65) Prior Publication Data
US 2016/0297143 A1  Oct. 13, 2016

(30) Foreign Application Priority Data

Jan. 16, 2014  (WO) ...................... PCT/2014/050841

(51) Int. Cl.
*B29C 67/00* (2017.01)
*B29C 67/04* (2017.01)
(Continued)

(52) U.S. Cl.
CPC .......... *B29C 67/0081* (2013.01); *A01N 43/80* (2013.01); *B29C 64/00* (2017.08);
(Continued)

(58) Field of Classification Search
None
See application file for complete search history.

(56) References Cited

U.S. PATENT DOCUMENTS 5,006,364 A    4/1991  Fan
5,342,919 A    8/1994  Dickens, Jr. et al.
(Continued)

FOREIGN PATENT DOCUMENTS

CN    1051627    5/1991
CN    1500608    6/2004
(Continued)

OTHER PUBLICATIONS

Wikipedia entry for Phthalocyanine (Year: 2019).*
(Continued)

*Primary Examiner* — Ramsey Zacharia
(74) *Attorney, Agent, or Firm* — Dierker & Kavanaugh PC

(57) ABSTRACT

In a 3D printing method, a coalescent dispersion for forming a 3D object is selected. The dispersion includes an aqueous vehicle and an infrared or near-infrared binding agent dissolved or dispersed therein. The binding agent is a phthalocyanine having a polar group attached to each side chain or a naphthalocyanine having a polar group attached to each side chain. A sinterable material is deposited and heated to a temperature ranging from about 50 C to about 350 C. The dispersion is selectively applied on at least a portion of the sinterable material. The sinterable material and the dispersion applied thereon are exposed to infrared or near-infrared radiation. The binding agent absorbs the radiation and converts it to thermal energy. At least the portion of the sinterable material in contact with the binding agent is at least cured to form a first layer of the 3D object.

18 Claims, 4 Drawing Sheets

(51) Int. Cl.

| | | |
|---|---|---|
| *B33Y 10/00* | (2015.01) | |
| *B33Y 70/00* | (2020.01) | |
| *B29C 64/165* | (2017.01) | |
| *B29C 64/386* | (2017.01) | |
| *B29C 64/40* | (2017.01) | |
| *B29C 64/00* | (2017.01) | |
| *A01N 43/80* | (2006.01) | |
| *C09B 47/04* | (2006.01) | |
| *B29K 105/16* | (2006.01) | |

(52) U.S. Cl.
CPC .......... *B29C 64/165* (2017.08); *B29C 64/386* (2017.08); *B29C 64/40* (2017.08); *B33Y 10/00* (2014.12); *B33Y 70/00* (2014.12); *C09B 47/045* (2013.01); *B29K 2049/00* (2013.01); *B29K 2105/16* (2013.01)

(56) References Cited

U.S. PATENT DOCUMENTS

| | | | |
|---|---|---|---|
| 5,514,519 | A | 5/1996 | Neckers |
| 6,596,224 | B1 | 7/2003 | Sachs et al. |
| 6,799,959 | B1 | 10/2004 | Tochimoto et al. |
| 7,470,315 | B2 | 12/2008 | Vonwiller et al. |
| 7,559,983 | B2 | 7/2009 | Starling et al. |
| 7,674,423 | B2 | 3/2010 | Sano |
| 7,959,724 | B2 | 6/2011 | Vonwiller et al. |
| 8,047,251 | B2 | 11/2011 | Khoshnevis |
| 8,110,135 | B2 | 2/2012 | El-Siblani |
| 8,142,860 | B2 | 3/2012 | Vanmaele et al. |
| 2004/0200816 | A1 | 10/2004 | Chung et al. |
| 2005/0003189 | A1 | 1/2005 | Bredt et al. |
| 2005/0080191 | A1 | 4/2005 | Kramer et al. |
| 2006/0018942 | A1 | 1/2006 | Rowe et al. |
| 2007/0238056 | A1 | 10/2007 | Baumann et al. |
| 2007/0241482 | A1 | 10/2007 | Giller et al. |
| 2009/0068580 | A1* | 3/2009 | Rimoto .................. B82Y 30/00 430/108.11 |
| 2010/0003470 | A1* | 1/2010 | Vonwiller .............. B41J 2/1404 428/195.1 |
| 2010/0244333 | A1 | 9/2010 | Bedal et al. |
| 2011/0130489 | A1 | 6/2011 | Williams |
| 2011/0204234 | A1 | 8/2011 | Ganapathiappan |
| 2012/0258250 | A1 | 10/2012 | Rodgers |

FOREIGN PATENT DOCUMENTS

| | | |
|---|---|---|
| CN | 103231513 | 8/2013 |
| EP | 0911142 | 4/1999 |
| EP | 1452298 | 9/2004 |
| EP | 1505111 | 2/2005 |
| EP | 2463081 | 6/2012 |
| JP | 6135915 | 2/1986 |
| WO | WO 9501257 | 1/1995 |
| WO | WO 0140874 | 6/2001 |
| WO | WO 2006/091842 | 8/2006 |
| WO | WO2007147625 | 12/2007 |
| WO | WO 2008/151063 | 12/2008 |
| WO | WO 2013021173 | 2/2013 |
| WO | WO 2013/030064 | 3/2013 |
| WO | WO 2013090174 | 6/2013 |

OTHER PUBLICATIONS

Akdemir, N.et al. "Synthesis and properties of 1,4-bis[N-(2-tolylsulphonylaminoethyl)]-1,4 diazacyclohexane bridged network polymeric phthalocyanines", Dyes & Pigments 69 2006.

Goodridge, R.D. et al., Laser Sintering of Polyamides and Other Polymers (Research Paper), Progress in Materials Science, Feb. 2012, pp. 229-267, vol. 57, Issue 2.

International Search Report and Written Opinion for International Application No. PCT/EP2014/050841 dated Sep. 25, 2014, 12 pages.

International Search Report and Written Opinion for International Application No. PCT/US2014/013511 dated Oct. 15, 2014, 9 pages.

International Search Report and Written Opinion for International Application No. PCT/US2014/013517 dated Oct. 23, 2014, 11 pages.

Particle Design for Performance, Cabot Corporation, 1995-2013, 4pages http://www.cabot-corp.com/.

Wimpenny, D.I. et al.; "Selective Infrared Sintering of Polymeric Powders using Radiant IR Heating & Ink Jet Printing"; DeMontfort University, Sep. 14, 2006; 11 pages.

* cited by examiner

THREE-DIMENSIONAL (3D) PRINTING METHOD

CROSS-REFERENCE TO RELATED APPLICATIONS

The present application claims the priority of International Application No. PCT/EP2014/050841 filed Jan. 16, 2014, the contents of which are hereby incorporated by reference.

BACKGROUND

Three-dimensional (3D) printing is an additive printing process used to make three-dimensional solid objects from a digital model. 3D printing is often used in rapid product prototyping, mold generation, and mold master generation. 3D printing techniques are considered additive processes because they involve the application of successive layers of material. This is unlike traditional machining processes, which often rely upon the removal of material to create the final object. Materials used in 3D printing often require curing or fusing, which for some materials may be accomplished using heat-assisted extrusion or sintering, and for other materials may be accomplished using digital light projection technology.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Examples of the three-dimensional (3D) printing method disclosed herein utilize light area processing. During light area processing, an entire layer of a sinterable material is exposed to radiation, but only a selected region of the sinterable material is fused and hardened to become a layer of a 3D object. In the examples disclosed herein, a coalescent dispersion is selectively deposited in contact with the selected region of the sinterable material. The coalescent dispersion(s) disclosed herein includes a water-soluble or a water-dispersible infrared or near-infrared binding agent, which is capable of penetrating into the layer of the sinterable material and passivating onto the exterior surface of the sinterable material. This binding agent is capable of absorbing radiation and converting the absorbed radiation to thermal energy, which in turn melts or sinters the sinterable material that is in contact with the binding agent. This causes the sinterable material to fuse, bind, cure, etc. to form the layer of the 3D object.

Figure 1:
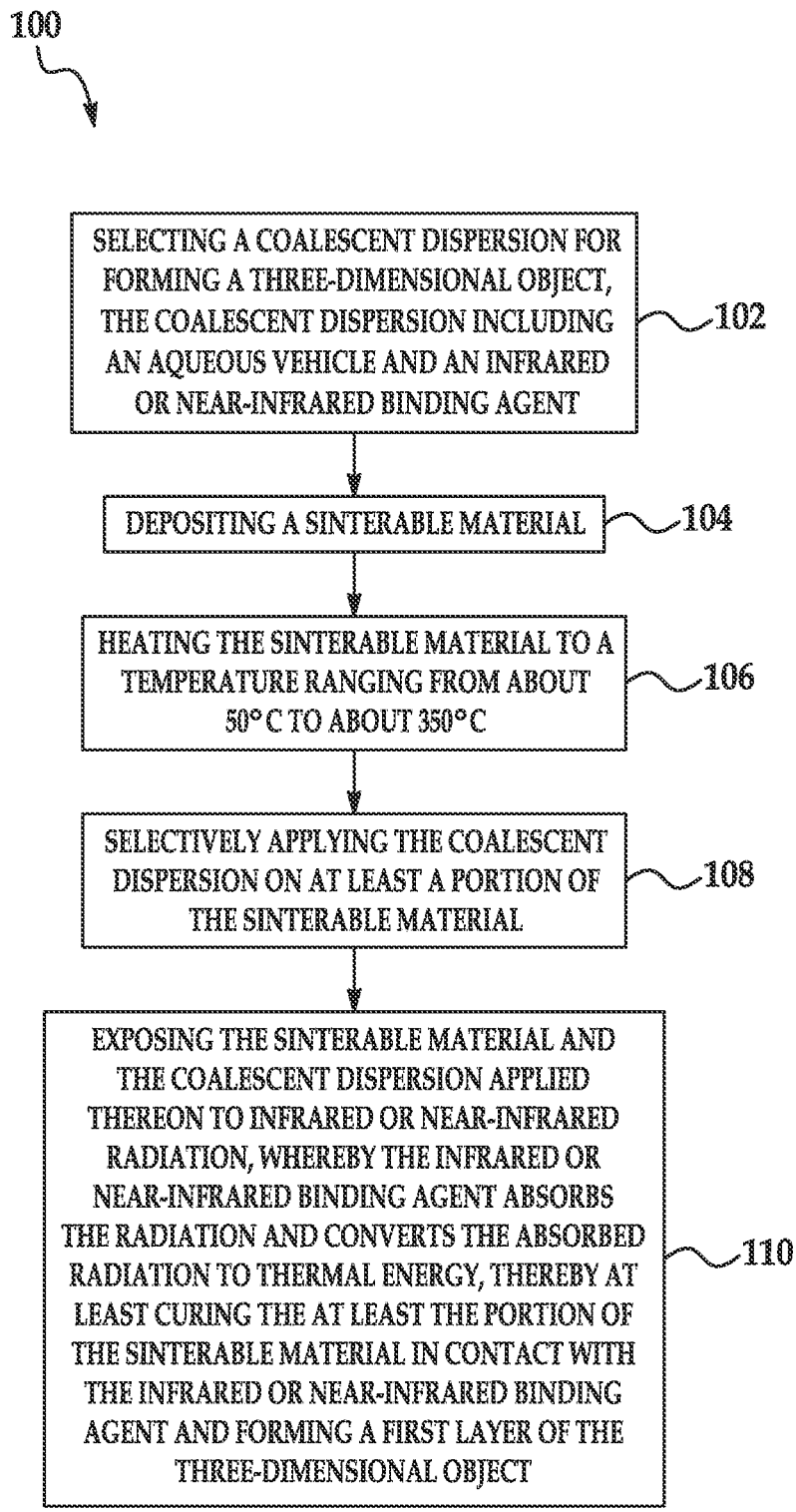
FIG. 1 is a flow diagram illustrating an example of a 3D printing method disclosed herein.

An example of the 3D printing method 100 is depicted in FIG. 1. It is to be understood that each of the steps of the method 100 shown in FIG. 1 will be discussed in detail herein, and in some instances, FIGS. 2A through 2E will be discussed in conjunction with FIG. 1.

As shown at reference number 102 in FIG. 1, an example of the method 100 includes selecting a coalescent dispersion for forming the 3D object. The coalescent dispersion includes an aqueous vehicle and the water-soluble or the water-dispersible infrared or near-infrared binding agent.

The aqueous vehicle may be water alone, or a combination of water and at least one co-solvent. When a co-solvent is used, it may be selected from any water-soluble organic solvent, such as 2-pyrrolidone, N-methylpyrrolidone, ethylene glycol, glycerol, 1,3-propanediol, 2-methylpropanediol, 1,4-butanediol, morpholine, N-methylmorpholine, and combinations thereof. In an example, the total amount of co-solvent(s) may range from about 1 wt % to about 40 wt % with respect to a total weight of the coalescent dispersion. In another example, the total amount of co-solvent(s) may range from about 1 wt % to about 20 wt % with respect to the total weight of the coalescent dispersion. In any example of the coalescent dispersion, the amount of water used makes up a balance of the dispersion (i.e., so a total wt % of the dispersion is 100).

The water-soluble or water-dispersible infrared or near-infrared binding agent is chemically inert and is capable of absorbing infrared or near-infrared radiation and converting the absorbed radiation to thermal energy. The water-soluble or water-dispersible infrared or near-infrared binding agent is also thermally stable (e.g., to temperatures up to at least 450° C.) over a wide pH range. It is believed that a rigid ring network of the water-soluble or water-dispersible infrared or near-infrared binding agent contributes to this stability.

The amount of the water-soluble or water-dispersible infrared or near-infrared binding agent that is present in the dispersion ranges from about 0.1 wt % to about 50 wt % with respect to the total weight of the coalescent dispersion.

Examples of the water-soluble or water-dispersible infrared or near-infrared binding agent include a naphthalocyanine with water-soluble substituents attached to each side chain thereof or a phthalocyanine with water-soluble substituents attached to each side chain thereof. Examples of the water-soluble substituents include highly polar groups, such as phosphates, ethylene oxide, or sulfonates. The attachment of the water-soluble substituents renders the naphthalocyanine or the phthalocyanine absorbent completely miscible with the aqueous vehicle.

In addition, the attachment of the water-soluble substituents renders the naphthalocyanine or the phthalocyanine absorbent to wavelengths ranging from 700 nm to 1000 nm.

In an example, the water-soluble substituents may be attached to the naphthalocyanine or the phthalocyanine by mixing the naphthalocyanine or the phthalocyanine with sulfuric acid and sulfur trioxide (to introduce sulfonate groups) at a temperature ranging from about 0° C. to about 50° C. The mixture may be poured into ice and centrifuged to isolate any precipitated material. The supernatant may be decanted and the remaining material may be neutralized to a desired pH (e.g., from about 7 to about 7.3). The neutralized material may be dialyzed against water to obtain the final product.

In another example, phosphonate water-soluble substituents may be attached to the naphthalocyanine or the phthalocyanine by treating the naphthalocyanine or the phthalocyanine with phosphoric anhydride at elevated temperatures ranging from about 100° C. to 250° C. The treated naphthalocyanine or phthalocyanine is then mixed with water and the mixture is treated at a temperature ranging from about 0° C. to about 50° C. The mixture may be poured into ice and centrifuged to isolate any precipitated material. The supernatant may be decanted and the remaining material may be neutralized to a desired pH (e.g., from about 7 to about 7.3). The neutralized material may be dialyzed against water to obtain the final product. In another example, diethyl phosphonate pthalocyanine is prepared and then the ethyl group is hydrolyzed using standard processing to generate phthalocyanine with phosphate groups.

In still another example, ethylene oxide groups may be introduced by first forming hydroxyl groups, and then treating with ethylene oxide. Hydroxyl groups can be introduced either before forming the phthalocyanine, or after forming the phthalocyanine with the corresponding acetate protecting groups and then regenerating the hydroxyl groups. Alternatively, a precursor containing ethylene oxide can be made and then the phthalocyanine ring can be directly obtained with the ethylene oxide units.

An example of the structure of the water-soluble substituted naphthalocyanine is shown below:

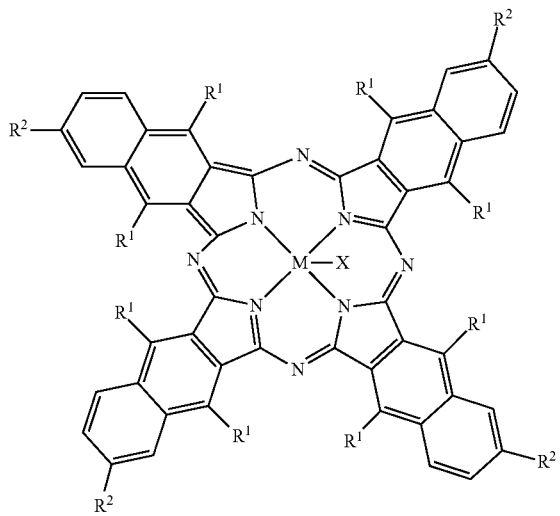

wherein $R^1$ is H, a $C_1$-$C_{18}$ alkoxy group, or $NH_2$; M is selected from the group consisting of Cu, Ti, Zn, Al, Fe, Co, Ga, In, Mn, Y, and Si; and $R^2$ is selected from the group consisting of a sulfonate, a phosphate, and an ethylene oxide. It is to be understood that X is present when M is more than divalent, and X is selected from the group consisting of a halogen; OH; OCOR, where R is H or a $C_1$-$C_{18}$ alkyl group; COOZ, where Z is Li, Na, or K; $SO_3Z$, where Z is Li, Na, or K; $PO_3Z$, where Z is Li, Na, or K; $NR^3_4{}^+$, where $R^3$ is H or a $C_1$-$C_{18}$ alkyl group; and $O(CH_2CH_2O)_mCH_3$, where m=1 to 500. A few water-soluble substituted naphthalocyanine structures include:

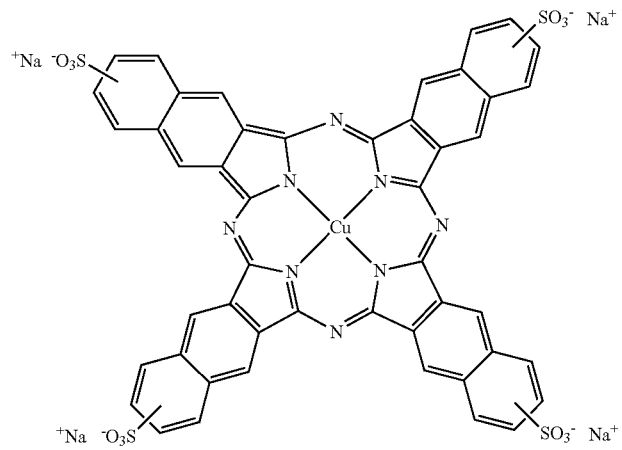

-continued
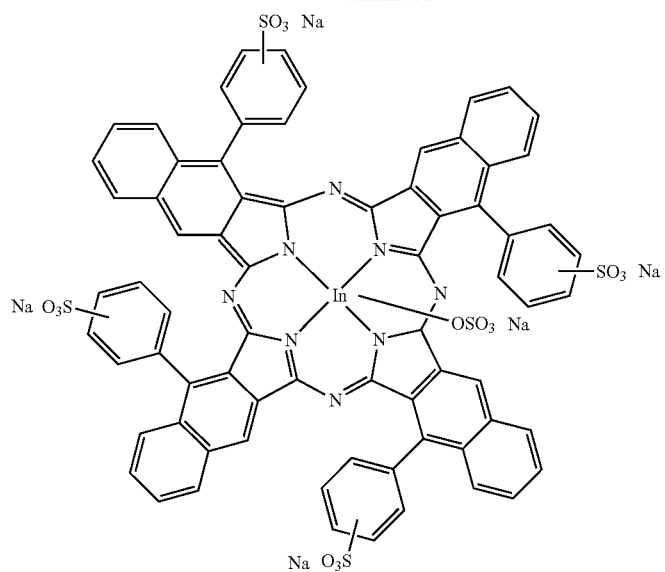
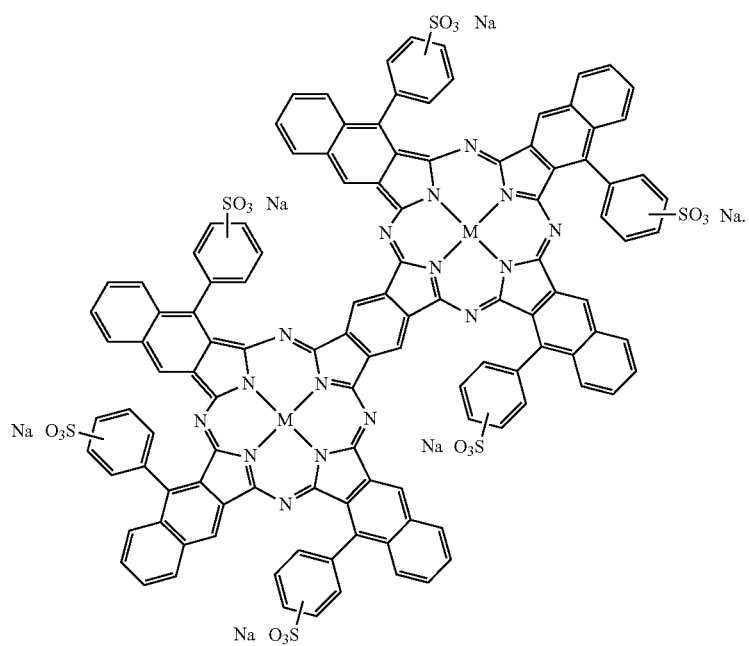

As illustrated, counter ions may also be present (e.g., sodium, potassium, or ammonium).

An example of the structure of the water-soluble substituted phthalocyanine is shown below:

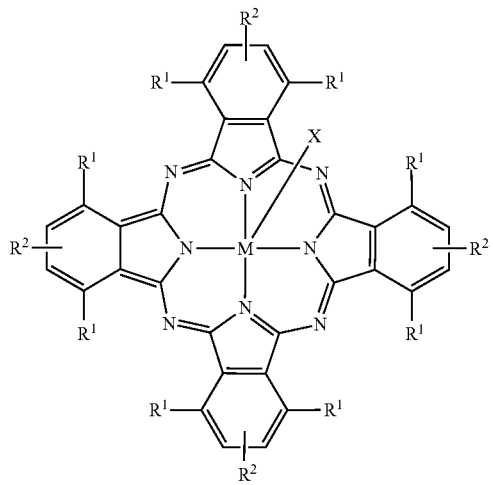

wherein $R^1$ is H, a $C_1$-$C_{18}$ alkoxy group, or $NH_2$; M is selected from the group consisting of In, Tl, Y, and Sc; and $R^2$ is selected from the group consisting of a sulfonate, a phosphate, and an ethylene oxide. It is again to be understood that X is present when M is more than divalent, and X is selected from the group consisting of a halogen; OH; OCOR, where R is H or a $C_1$-$C_{18}$ alkyl group; COOZ, where Z is Li, Na, or K; $SO_3Z$, where Z is Li, Na, or K; $PO_3Z$, where Z is Li, Na, or K; $NR^3_4{}^+$, where $R^3$ is H or a $C_1$-$C_{18}$ alkyl group; and $O(CH_2CH_2O)_mCH_3$, where m=1 to 500. It is to be understood that sodium, potassium, or ammonium counter ions may also be present.

A few specific examples of the water-soluble or water-dispersible infrared or near-infrared binding agent include copper naphthalocyanine sulfonate and indium phthalocyanine sulfonate.

In some examples, the coalescent dispersion consists of the aqueous vehicle and the binding agent alone. In other examples, the coalescent dispersion includes a surfactant, a biocide, a gloss enhancing agent, a pigment, and/or combinations thereof.

A surfactant may be added in order to control the wetting angle (i.e., surface energy) of the coalescent dispersion. An example of a suitable surfactant includes sodium dodecylsulfate. When used, the surfactant amount may range from about 0.5 wt % to about 40 wt % with respect to the total weight of the coalescent dispersion.

The biocide may be added in any amount ranging from about 0.1 wt % to about 1 wt % with respect to the total weight of the coalescent dispersion. An example of a suitable biocide includes PROXEL™ GXL (an aqueous solution of 1,2-benzisothiazolin-3-one, available from Arch Chemicals, Inc.).

When it is desirable that at least a portion of the 3D object be glossy, the coalescent dispersion may include a gloss enhancing agent. Examples of suitable gloss enhancing agents include wax and long chain hydrocarbons (i.e., molecules with 16 or more carbon atoms, such as isohexadecane, or 20 or more carbon atoms). The gloss enhancing agent may be present in an amount ranging from about 1 wt % to about 25 wt % with respect to the total weight of the coalescent dispersion. As will be discussed further in reference to reference number 108, examples of the coalescent dispersion including the gloss enhancing agent may be used to form the entire 3D object, the perimeter of the 3D object, portions of the perimeter of the 3D object, etc.

In the absence of an additional colored pigment, the coalescent dispersion has a transparent (or nearly transparent) visual appearance. In these instances, the resulting 3D object will have no color, or a color that resembles the natural color of the sinterable material. In other instances, a pigment may be added in order to impart color to the coalescent dispersion, and to the layer or the portion of the 3D object made with the pigmented/colored coalescent dispersion.

When used, the pigment may be added to the coalescent dispersion in an amount ranging from about 1 wt % to about 10 wt % with respect to the total weight of the coalescent dispersion. The pigment may be any color, including, as examples, a cyan pigment, a magenta pigment, a yellow pigment, a black pigment, a violet pigment, a green pigment, a brown pigment, an orange pigment, a purple pigment, a white pigment, a metallic pigment (e.g., a gold pigment, a bronze pigment, a silver pigment, or a bronze pigment), a pearlescent pigment, or combinations thereof. Organic and/or inorganic pigments may be used.

Examples of blue or cyan organic pigments include C.I. Pigment Blue 1, C.I. Pigment Blue 2, C.I. Pigment Blue 3, C.I. Pigment Blue 15, C.I. Pigment Blue 15:3, C.I. Pigment Blue 15:34, C.I. Pigment Blue 15:4, C.I. Pigment Blue 16, C.I. Pigment Blue 18, C.I. Pigment Blue 22, C.I. Pigment Blue 25, C.I. Pigment Blue 60, C.I. Pigment Blue 65, C.I. Pigment Blue 66, C.I. Vat Blue 4, and C.I. Vat Blue 60.

Some examples of suitable magenta, red, or violet organic pigments include C.I. Pigment Red 1, C.I. Pigment Red 2, C.I. Pigment Red 3, C.I. Pigment Red 4, C.I. Pigment Red 5, C.I. Pigment Red 6, C.I. Pigment Red 7, C.I. Pigment Red 8, C.I. Pigment Red 9, C.I. Pigment Red 10, C.I. Pigment Red 11, C.I. Pigment Red 12, C.I. Pigment Red 14, C.I. Pigment Red 15, C.I. Pigment Red 16, C.I. Pigment Red 17, C.I. Pigment Red 18, C.I. Pigment Red 19, C.I. Pigment Red 21, C.I. Pigment Red 22, C.I. Pigment Red 23, C.I. Pigment Red 30, C.I. Pigment Red 31, C.I. Pigment Red 32, C.I. Pigment Red 37, C.I. Pigment Red 38, C.I. Pigment Red 40, C.I. Pigment Red 41, C.I. Pigment Red 42, C.I. Pigment Red 48(Ca), C.I. Pigment Red 48(Mn), C.I. Pigment Red 57(Ca), C.I. Pigment Red 57:1, C.I. Pigment Red 88, C.I. Pigment Red 112, C.I. Pigment Red 114, C.I. Pigment Red 122, C.I. Pigment Red 123, C.I. Pigment Red 144, C.I. Pigment Red 146, C.I. Pigment Red 149, C.I. Pigment Red 150, C.I. Pigment Red 166, C.I. Pigment Red 168, C.I. Pigment Red 170, C.I. Pigment Red 171, C.I. Pigment Red 175, C.I. Pigment Red 176, C.I. Pigment Red 177, C.I. Pigment Red 178, C.I. Pigment Red 179, C.I. Pigment Red 184, C.I. Pigment Red 185, C.I. Pigment Red 187, C.I. Pigment Red 202, C.I. Pigment Red 209, C.I. Pigment Red 219, C.I. Pigment Red 224, C.I. Pigment Red 245, C.I. Pigment Violet 19, C.I. Pigment Violet 23, C.I. Pigment Violet 32, C.I. Pigment Violet 33, C.I. Pigment Violet 36, C.I. Pigment Violet 38, C.I. Pigment Violet 43, and C.I. Pigment Violet 50.

Some examples of suitable yellow organic pigments include C.I. Pigment Yellow 1, C.I. Pigment Yellow 2, C.I. Pigment Yellow 3, C.I. Pigment Yellow 4, C.I. Pigment Yellow 5, C.I. Pigment Yellow 6, C.I. Pigment Yellow 7, C.I. Pigment Yellow 10, C.I. Pigment Yellow 11, C.I. Pigment Yellow 12, C.I. Pigment Yellow 13, C.I. Pigment Yellow 14, C.I. Pigment Yellow 16, C.I. Pigment Yellow 17, C.I.

Pigment Yellow 24, C.I. Pigment Yellow 34, C.I. Pigment Yellow 35, C.I. Pigment Yellow 37, C.I. Pigment Yellow 53, C.I. Pigment Yellow 55, C.I. Pigment Yellow 65, C.I. Pigment Yellow 73, C.I. Pigment Yellow 74, C.I. Pigment Yellow 75, C.I. Pigment Yellow 81, C.I. Pigment Yellow 83, C.I. Pigment Yellow 93, C.I. Pigment Yellow 94, C.I. Pigment Yellow 95, C.I. Pigment Yellow 97, C.I. Pigment Yellow 98, C.I. Pigment Yellow 99, C.I. Pigment Yellow 108, C.I. Pigment Yellow 109, C.I. Pigment Yellow 110, C.I. Pigment Yellow 113, C.I. Pigment Yellow 114, C.I. Pigment Yellow 117, C.I. Pigment Yellow 120, C.I. Pigment Yellow 124, C.I. Pigment Yellow 128, C.I. Pigment Yellow 129, C.I. Pigment Yellow 133, C.I. Pigment Yellow 138, C.I. Pigment Yellow 139, C.I. Pigment Yellow 147, C.I. Pigment Yellow 151, C.I. Pigment Yellow 153, C.I. Pigment Yellow 154, C.I. Pigment Yellow 167, C.I. Pigment Yellow 172, C.I. Pigment Yellow 180, and C.I. Pigment Yellow 185.

An example of a suitable inorganic black pigment includes carbon black. Examples of carbon black pigments include those manufactured by Mitsubishi Chemical Corporation, Japan (such as, e.g., carbon black No. 2300, No. 900, MCF88, No. 33, No. 40, No. 45, No. 52, MA7, MA8, MA100, and No. 2200B); various carbon black pigments of the RAVEN® series manufactured by Columbian Chemicals Company, Marietta, Ga., (such as, e.g., RAVEN® 5750, RAVEN® 5250, RAVEN® 5000, RAVEN® 3500, RAVEN® 1255, and RAVEN® 700); various carbon black pigments of the REGAL® series, the MOGUL® series, or the MONARCH® series manufactured by Cabot Corporation, Boston, Mass., (such as, e.g., REGAL® 400R, REGAL® 330R, and REGAL® 660R); and various black pigments manufactured by Evonik Degussa Corporation, Parsippany, N.J. (such as, e.g., Color Black FW1, Color Black FW2, Color Black FW2V, Color Black FW18, Color Black FW200, Color Black S150, Color Black S160, Color Black S170, PRINTEX® 35, PRINTEX® U, PRINTEX® V, PRINTEX® 140U, Special Black 5, Special Black 4A, and Special Black 4). An example of an organic black pigment includes aniline black, such as C.I. Pigment Black 1.

Some examples of green organic pigments include C.I. Pigment Green 1, C.I. Pigment Green 2, C.I. Pigment Green 4, C.I. Pigment Green 7, C.I. Pigment Green 8, C.I. Pigment Green 10, C.I. Pigment Green 36, and C.I. Pigment Green 45.

Examples of brown organic pigments include C.I. Pigment Brown 1, C.I. Pigment Brown 5, C.I. Pigment Brown 22, C.I. Pigment Brown 23, C.I. Pigment Brown 25, C.I. Pigment Brown 41, and C.I. Pigment Brown 42.

Some examples of orange organic pigments include C.I. Pigment Orange 1, C.I. Pigment Orange 2, C.I. Pigment Orange 5, C.I. Pigment Orange 7, C.I. Pigment Orange 13, C.I. Pigment Orange 15, C.I. Pigment Orange 16, C.I. Pigment Orange 17, C.I. Pigment Orange 19, C.I. Pigment Orange 24, C.I. Pigment Orange 34, C.I. Pigment Orange 36, C.I. Pigment Orange 38, C.I. Pigment Orange 40, C.I. Pigment Orange 43, and C.I. Pigment Orange 66.

A suitable metallic pigment includes a metal chosen from gold, silver, platinum, nickel, chromium, tin, zinc, indium, titanium, copper, aluminum, and alloys of any of these metals. These metals may be used alone or in combination with two or more metals or metal alloys. Some examples of metallic pigments include STANDART® RO100, STANDART® RO200, and DORADO® gold-bronze pigments (available from Eckart Effect Pigments, Wesel, Germany).

When the coalescent dispersion includes a pigment, it may be desirable to also include a dispersant. The dispersant selected may be capable of dispersing the pigment throughout the aqueous vehicle. An example of a suitable dispersant includes sodium dodecylsulfate. The amount of dispersant included will depend on the amount of pigment used, and may range from about 1 wt % to about 20 wt % with respect to the total weight of the pigment in the coalescent dispersion. If the pigment is a self-dispersible pigment, an additional dispersant will not be used.

After the coalescent dispersion is selected, the method 100 further includes depositing a sinterable material, as shown at reference number 104 of FIG. 1. An example of this step 104 is shown in cross-section at FIG. 2A. In the example shown in FIG. 2A, one layer 10 of the sinterable material 16 has been deposited, as will be discussed in more detail below.

The sinterable material 16 may be a powder, a liquid, a paste, or a gel. Examples of sinterable material 16 include semi-crystalline thermoplastic materials with a wide processing window of greater than 5° C. (i.e., the temperature range between the melting point and the re-crystallization temperature). Some specific examples of the sinterable material 16 include polyamides (e.g., nylon 11, nylon 12, nylon 6, nylon 8, nylon 9, nylon 66, nylon 612, nylon 812, nylon 912, etc.). Other specific examples of the sinterable material 16 include polyethylene, polyethylene terephthalate (PET), and amorphous variation of these materials.

Figure 2A:
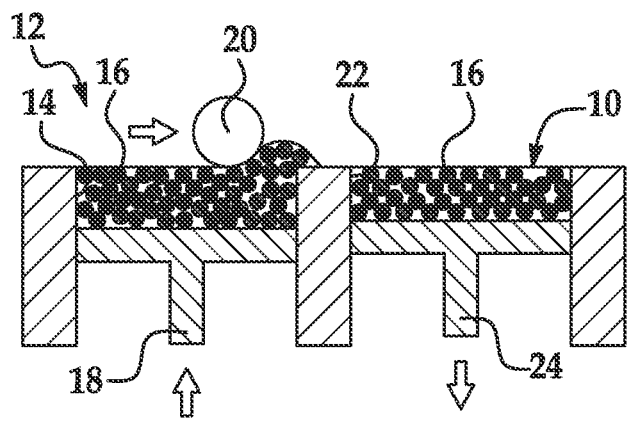
FIGS. 2A through 2E are cross-sectional views of the steps involved in forming one layer of a 3D object using an example of the 3D printing method disclosed herein.

In the example shown in FIG. 2A, a printing for forming the 3D object includes a supply bed 14 (including a supply of the sinterable material 16), a delivery piston 18, a roller 20, a fabrication bed 22, and a fabrication piston 24. Each of these physical elements may be operatively connected to a central processing unit (not shown) of the printing system 12. The central processing unit (e.g., running computer readable instructions stored on a non-transitory, tangible computer readable storage medium) manipulates and transforms data represented as physical (electronic) quantities within the printer's registers and memories in order to control the physical elements to create the 3D object. The data for the selective delivery of the sinterable material 16, the coalescent dispersion, etc. may be derived from a model of the 3D object to be formed.

The delivery piston 18 and the fabrication piston 24 may be the same type of piston, but are programmed to move in opposite directions. In an example, when a first layer of the 3D object is to be formed, the delivery piston 18 may be programmed to push a predetermined amount of the sinterable material 16 out of the opening in the supply bed 14 and the fabrication piston 24 may be programmed to move in the opposite direction of the delivery piston 18 in order to increase the depth of the fabrication bed 22. The delivery piston 18 will advance enough so that when the roller 20 pushes the sinterable material 16 into the fabrication bed 22, the depth of the fabrication bed 22 is sufficient so that a layer 10 of the sinterable material 16 may be formed in the bed 22. The roller 20 is capable of spreading the sinterable material 16 into the fabrication bed 22 to form the layer 10, which is relatively uniform in thickness. In an example, the thickness of the layer 10 ranges from about 90 μm to about 110 μm, although thinner or thicker layers may also be used.

It is to be understood that the roller 20 may be replaced by other tools, such as a blade that may be desirable for spreading different types of powders, or a combination of a roller and a blade.

Figure 2B:
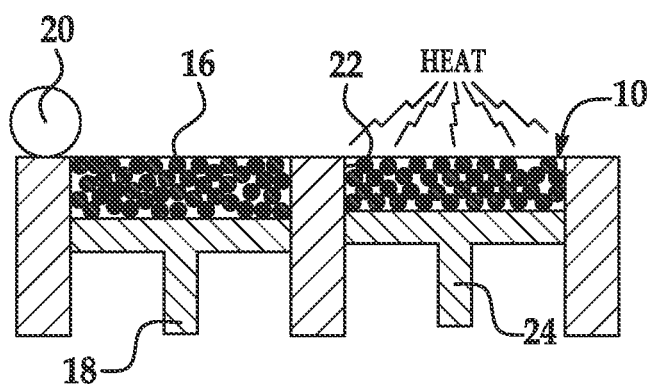

After the layer 10 of the sinterable material 16 is deposited in the fabrication bed 22, the layer 10 is exposed to heating (as shown at reference number 104 in FIG. 1 and in FIG. 2B). Heating is performed to pre-heat the sinterable material 16, and thus it is desirable that the heating temperature be below the melting point of the sinterable material 16. As such, the temperature selected will depend upon the sinterable material 16 that is used. As examples, the heating temperature may be from about 5° C. to about 50° C. below the melting point of the sinterable material. In an example, the heating temperature ranges from about 50° C. to about 350° C. as shown at reference number 106 in FIG. 1). In another example, the heating temperature ranges from about 60° C. to about 170° C.

Pre-heating the layer 10 of the sinterable material 16 may be accomplished using any suitable heat source that exposes all of the sinterable material 16 in the fabrication bed 22 to the heat. Examples of the heat source include a thermal heat source or a light radiation source.

Figure 2C:
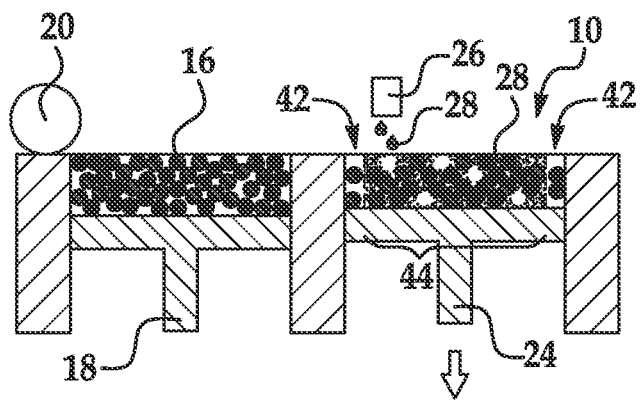
Figure 2D:
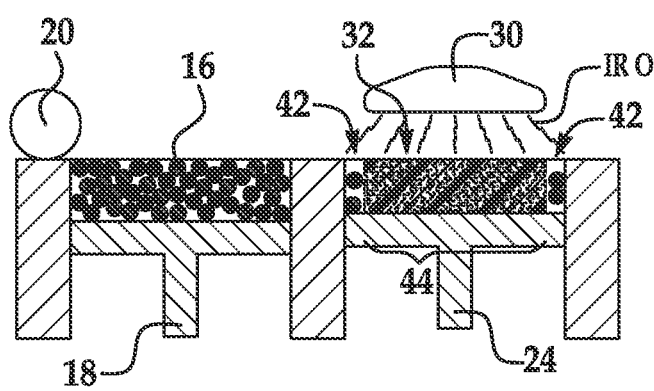

After pre-heating the layer 10, the coalescent dispersion is selectively applied on at least a portion of the sinterable material 16 in the layer 10, as shown at reference number 108 in FIG. 1 and in FIG. 2C. As illustrated in FIG. 2C, the coalescent dispersion 28 may be dispensed from an inkjet printhead 26. While a single printhead is shown in FIG. 2C, it is to be understood that multiple printheads may be used that span the width of the fabrication bed 22. The printhead 26 may be attached to a moving XY stage or a translational carriage (neither of which is shown) that moves the printhead 26 adjacent to the fabrication bed 22 in order to deposit the coalescent dispersion 28 in desirable area(s). The printhead 26 may be programmed to receive commands from the central processing unit and to deposit the coalescent dispersion 28 according to a pattern for the first layer of the 3D object. The printhead 26 selectively applies the coalescent dispersion 28 on those portions of the layer 10 that are to be fused to become the first layer of the 3D object. As an example, if the first layer is to be shaped like a cube or cylinder, the coalescent dispersion 28 will be deposited in a square pattern or a circular pattern (from a top view), respectively, on at least a portion of the layer 10 of the sinterable material 16. In the example shown in FIG. 2C, the coalescent dispersion 28 is deposited in a square pattern on the area 44 of the layer 10 and not on the areas 42.

The water soluble nature of the binding agent and the aqueous nature of the coalescent dispersion 28 enable the binding agent i) to penetrate into the sinterable material layer 10, even though the layer 10 may have varying compaction or porosity, and, in some instances, ii) to passivate the surfaces of the sinterable material 16. The sinterable material 10 may be hydrophobic, and the presence of the co-solvent and/or surfactant in the coalescent dispersion 28 may assist in obtaining desirable wetting behavior.

The integration of the binding agent throughout the portion of the layer 10 upon which the coalescent dispersion 28 is applied enables control over the mechanical functionality (by tweaking the amount of binding agent and thus controlling the level of sintering, fusing, binding in and between layers) and dimensional accuracy of the layer of the 3D object that is formed.

A single coalescent dispersion 28 may be selectively applied to form the layer of the 3D object, or multiple coalescent dispersions 28 may be selectively applied to form the layer of the 3D object.

In an example in which it is desirable that the entire layer of the 3D object be glossy, a single coalescent dispersion 28 including the gloss enhancing agent may be selectively applied. In this example, gloss will be imparted to both the interior and the exterior of the layer that is formed.

In another example in which it is desirable that the exterior of the 3D object be glossy, a coalescent dispersion 28 that does not include the gloss enhancing agent may be selectively applied to form the interior of the layer, and a second coalescent dispersion (not shown) including the gloss enhancing agent may be selectively applied along the outer edge or perimeter of the coalescent dispersion 28 that does not include the gloss enhancing agent. In these examples, enhanced gloss is exhibited at the exterior of the layer that is ultimately formed. In the example shown in FIG. 2C, the second coalescent dispersion including the gloss enhancing agent could be selectively applied in the areas 42 at the outer edge of the coalescent dispersion 28 without the gloss enhancing agent.

Figure 3A:
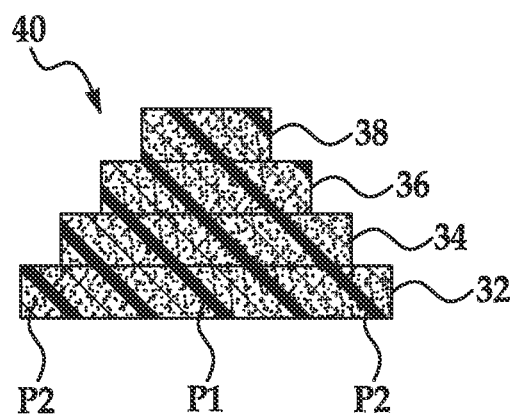
FIG. 3A is a cross-sectional view of an example of the 3D object formed using an example of the 3D printing method.
Figure 3B:
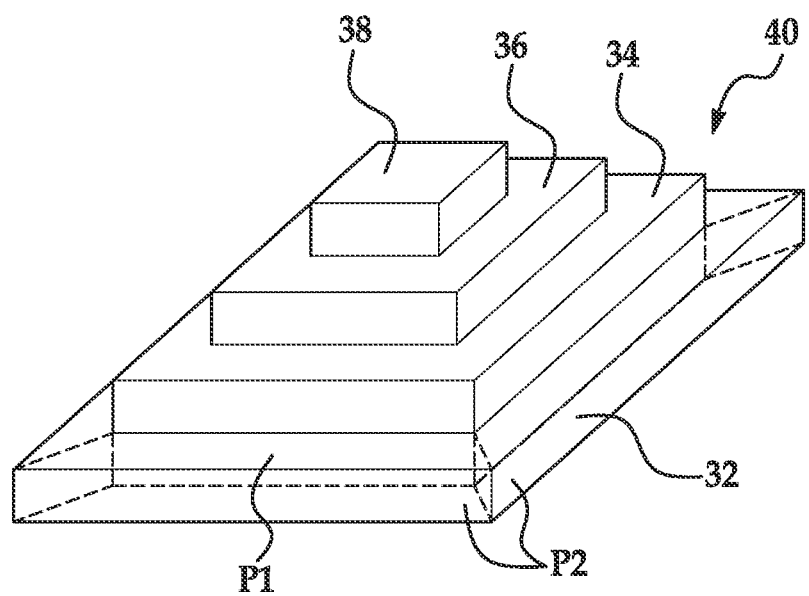
FIG. 3B is a perspective view of the 3D object of FIG. 3A.

Alternatively in the example shown in FIG. 2C, the second coalescent dispersion including the gloss enhancing agent could be selectively applied instead of the coalescent dispersion 28 to form the perimeter that is shown. An example of the layer 32 formed as a result of this process is shown in FIG. 3A. In making the layer 32, the interior portion P1 is made, in part, from the coalescent dispersion 28 that does not contain the gloss enhancing agent, and the exterior portion(s) P2 is made, in part, from the second coalescent dispersion that does contain the gloss enhancing agent. As depicted in FIG. 3B, the portion P2 with enhanced gloss will be visible in the final object 40 and the portion P1 without enhanced gloss forms the interior of the layer 32, which is not visible in the final object 40.

The gloss effect may be enhanced by increasing the voxel density of the coalescent dispersion including the gloss enhancing agent. For example, multiple drops of the coalescent dispersion including the gloss enhancing agent may be applied at each pixel/voxel site where enhanced gloss is desirable, or the width/spread of the coalescent dispersion including the gloss enhancing agent may be increased.

Furthermore, as the layers of the 3D object are built up in the Z-direction, uniformity or variations in gloss may be achieved along the XY plane and/or along the Z axis. Gloss uniformity may be achieved by applying the coalescent dispersion with the gloss enhancing agent at least at the perimeter of each of the respective layers at the same voxel density. In one example, gloss variations may be achieved by applying the coalescent dispersion with the gloss enhancing agent at least at the perimeter of each of the respective layers at different voxel densities. As an example, if it is desirable that gloss decrease along the Z axis, the voxel density of the coalescent dispersion with the gloss enhancing agent may be the highest in the first layer and decrease in subsequently formed layers. As another example, if it is desirable that gloss decrease along the X axis, the voxel density of the coalescent dispersion with the gloss enhancing agent may be the highest at the left (or right) side of each layer and decrease moving towards the right (or left) side of each layer. In another example, gloss variations may be achieved by applying the coalescent dispersion with the gloss enhancing agent at some regions and applying the coalescent dispersion without the gloss enhancing agent at other regions.

In an example in which it is desirable that the entire layer of the 3D object be some color (i.e., other than transparent) or the color of the sinterable material 16, a single coalescent dispersion 28 including pigment may be selectively applied. In this example, color will be imparted to both the interior and the exterior of the layer that is formed.

In another example in which it is desirable that the exterior of the 3D object be colored, a coalescent dispersion 28 that does not include the pigment may be selectively applied to form the interior of the layer, and a second coalescent dispersion (not shown) including the pigment may be selectively applied along the outer edge or perimeter of the coalescent dispersion 28 that does not include the pigment. In these examples, the pigment color (or a shade of the pigment color) is exhibited at the exterior of the layer that is ultimately formed. In the example shown in FIG. 2C, the second coalescent dispersion including the pigment could be selectively applied in the areas 42 at the outer edge of the coalescent dispersion 28 without the pigment.

Alternatively in the example shown in FIG. 2C, the second coalescent dispersion including the pigment could be selectively applied instead of the coalescent dispersion 28 (without pigment) to form the perimeter that is shown. An example of the layer 32 formed as a result of this process is shown in FIG. 3A. In making the layer 32, the interior portion P1 is made, in part, from the coalescent dispersion 28 that does not contain the pigment, and the exterior portion(s) P2 is made, in part, from the second coalescent dispersion that does contain the pigment. As depicted in FIG. 3B, the colored portion P2 will be visible in the final object 40 and the colorless portion P1 forms the interior of the layer 32, which is not visible in the final object 40.

As the layers of the 3D object are built up in the Z-direction, uniformity or variations in color may be achieved along the XY plane and/or along the Z axis. Color uniformity may be achieved by applying the coalescent dispersion of a single color at least at the perimeter of each of the respective layers at the same voxel density. Color variations may be achieved by selectively depositing different coalescent dispersions that contain differently colored pigments or the same colored pigments of different shades at different areas, or by selectively depositing different amounts of the same colored coalescent dispersion at different areas. In one example, color variations may be achieved by applying the coalescent dispersion with the pigment at least at the perimeter of each of the respective layers at different voxel densities. As an example, if it is desirable that color decrease along the Z axis, the voxel density of the coalescent dispersion with the pigment may be the highest in the first layer and decrease in subsequently formed layers. As another example, if it is desirable that color decrease along the X axis, the voxel density of the coalescent dispersion with the pigment may be the highest at the left (or right) side of each layer and decrease moving towards the right (or left) side of each layer. In another example, color variations may be achieved by applying the coalescent dispersion with the pigment at some regions and applying the coalescent dispersion without the pigment at other regions.

After the coalescent dispersion(s) 28 is/are selectively applied in the desired area(s), the entire layer 10 of the sinterable material 16 and the coalescent dispersion(s) 28 applied to at least a portion thereof are exposed to infrared or near-infrared radiation. This is shown at step 110 in FIG. 1 and in FIG. 2D.

The infrared or near-infrared radiation is emitted from a sintering source 30, such as an IR or near-IR curing lamp, IR or near-IR light emitting diodes (LED), or lasers with the desirable IR wavelengths. The sintering source 30 may be attached, for example, to a carriage that also holds the printhead(s) 26. The carriage may move the sintering source 30 into a position that is adjacent to the fabrication bed 22. The sintering source 30 may be programmed to receive commands from the central processing unit and to expose the layer 10 and coalescent dispersion 28 to IR or near-IR energy.

The length of time the radiation is applied for, or energy exposure time, may be dependent, for example, on one or more of: characteristics of the radiation source 40; characteristics of the sinterable material 16; and/or characteristics of the coalescent dispersion 28.

It is to be understood that variations in the sintering level may be achieved using similar strategies described above for gloss and/or color variations. As an example, if it is desirable that the level of sintering decrease along the Z axis, the radiation exposure time may be the highest in the first layer and decrease in subsequently formed layers.

The water-soluble or water-dispersible infrared or near-infrared binding agent in the coalescent dispersion 28 enhances the absorption of the IR or near-IR energy, converts the absorbed IR or near-IR energy to thermal energy, and promotes the transfer of the thermal heat to the sinterable material 16 in contact with the binding agent (i.e., in the area 44). In an example, the water-soluble or water-dispersible infrared or near-infrared binding agent sufficiently elevates the temperature of the sinterable material 16 in the area 44 above its melting point, allowing curing (e.g., sintering, binding, fusing, etc.) of the sinterable material 16 to take place. The coalescent dispersion 28 may also cause, for example, heating of the sinterable material 16 below its melting point but to a temperature suitable to cause softening and bonding. It is to be understood that area(s) 42 not having the coalescent dispersion 28 applied thereto absorb less energy, and thus the sinterable material 16 within these area(s) 42 generally does not exceed the melting point and does cure. This forms one layer 32 of the 3D object 40 (FIGS. 3A and 3B) to be formed.

As mentioned above, the exposure to the IR or near-IR radiation cures the sinterable material 16 in the area(s) 44 to form the layer 32 of the 3D object. Steps 104 through 110 of FIG. 1 may be repeated as many times as desirable to create subsequent layers 34, 36, 38 (FIG. 2E) and to ultimately form the 3D object 40. It is to be understood that heat absorbed during the application of energy from a portion of the sinterable material 16 on which coalescent dispersion 28 has been delivered or has penetrated may propagate to a previously solidified layer, such as layer 32, causing at least some of that layer to heat up above its melting point. This effect helps create strong interlayer bonding between adjacent layers of the 3D object 40.

Figure 2E:
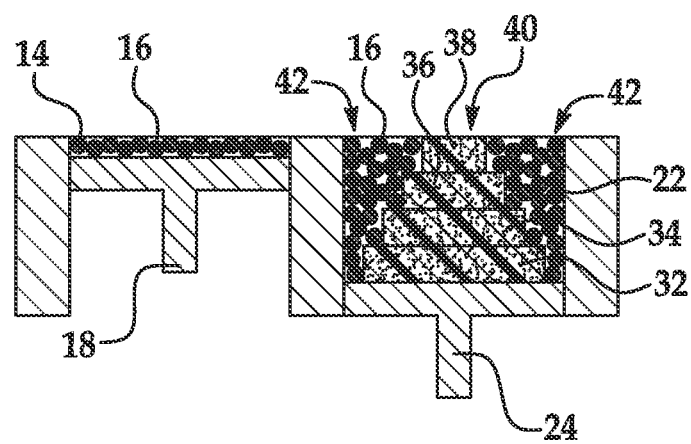

FIG. 2E illustrates one example of the 3D object 40. It is to be understood, however, that the subsequently formed layers 34, 36, 38 may have any desirable shape and/or thickness and may be the same as or different from any other layer 32, 34, 36, 38, depending upon the size, shape, etc. of the 3D object 40 that is to be formed.

As illustrated in FIG. 2E, as subsequent layers 34, 36, 38 have been formed, the delivery piston 18 is pushed closer to the opening of the delivery bed 14, and the supply of the sinterable material 16 in the delivery bed 14 is diminished (compared, for example, to FIG. 2A at the outset of the method). The fabrication piston 24 is pushed further away from the opening of the fabrication bed 22 in order to accommodate the subsequent layer(s) of sinterable material 16 and selectively applied coalescent dispersion 28. Since at least some of the sinterable material 16 remains uncured after each layer 32, 34, 36, 38 is formed, the 3D object 40 is at least partially surrounded by the uncured sinterable material 16 in the fabrication bed 22.

When the 3D object 40 is complete, it may be removed from the fabrication bed, and the uncured sinterable material 16 remaining in the fabrication bed 22 may be reused. The 3D object 40 may be treated with water in order to remove any uncured binding agent at the surface of the 3D object 40. Since the removed binding agent is water-soluble or water-dispersible, it may be recycled. In an example, the binding agent removed in the water treatment may be incorporated into another coalescent dispersion 28, which is used to form another 3D object.

As previously mentioned, FIGS. 3A and 3B illustrate a cross-sectional and perspective view of the 3D object 40. Each of the layers 32, 34, 36, 38 includes cured (sintered, fused, etc.) sinterable material and the infrared or near-infrared binding agent binding the cured sinterable material.

Figure 4:
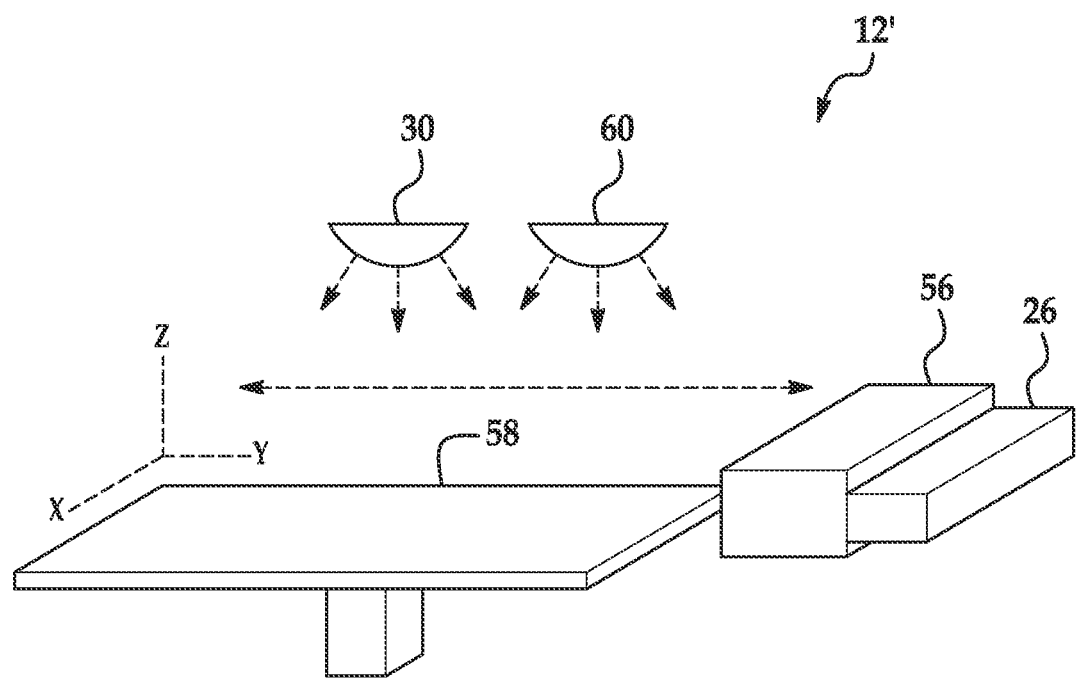
FIG. 4 is a simplified isometric view of an example of a 3D printing system that may be used in an example of the 3D printing method as disclosed herein.
Figure 4:
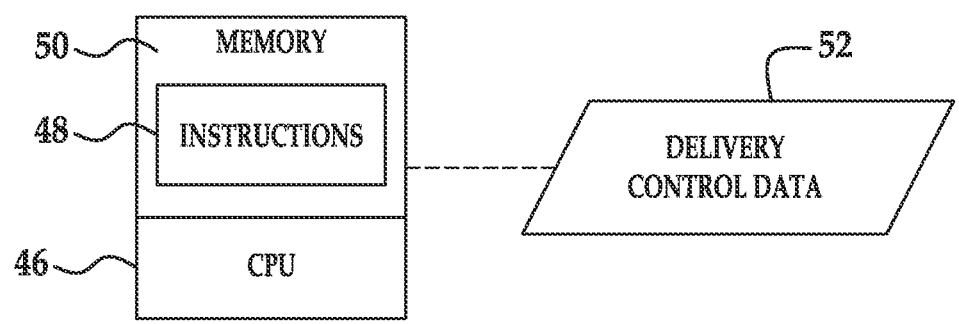

Referring now to FIG. 4, another example of the printing system 12' is depicted. The system 12' includes a central processing unit 46 that controls the general operation of the additive printing system 12'. As an example, the central processing unit 46 may be a microprocessor-based controller that is coupled to a memory 50, for example via a communications bus (not shown). The memory 50 stores the computer readable instructions 48. The central processing unit 46 may execute the instructions 48, and thus may control operation of the system 12' in accordance with the instructions 48.

In this example, the printing system 12' includes a coalescent dispersion distributor 26 to selectively deliver coalescent dispersion 28 to a layer (not shown in this figure) of sinterable material 16 provided on a support member 58. In an example, the support member 58 has dimensions ranging from about 10 cm by 10 cm up to about 100 cm by 100 cm, although the support member 58 may have larger or smaller dimensions depending upon the 3D object 40 that is to be formed.

The central processing unit 46 controls the selective delivery of the coalescent dispersion 28 to the layer of the sinterable material 16 in accordance with delivery control data 52.

In the example shown in FIG. 4, it is to be understood that the distributor 26 is a printhead, such as a thermal printhead or a piezoelectric inkjet printhead. The printhead 26 may be a drop-on-demand printhead or a continuous drop printhead.

The printhead 26 may be used to selectively deliver the coalescent dispersion 28 when in the form of a suitable fluid. As described above, the coalescent dispersion 28 includes the aqueous vehicle, such as water, co-solvent(s), dispersant (s), etc., to enable it to be delivered via the printhead 26.

In one example the printhead 26 may be selected to deliver drops of the coalescent dispersion 28 at a resolution ranging from about 300 dots per inch (DPI) to about 1200 DPI. In other examples, the printhead 26 may be selected to be able to deliver drops of the coalescent dispersion 28 at a higher or lower resolution.

The printhead 26 may include an array of nozzles through which the printhead 26 is able to selectively eject drops of fluid. In one example, each drop may be in the order of about 10 pico liters (pl) per drop, although it is contemplated that a higher or lower drop size may be used. In some examples, printhead 26 is able to deliver variable size drops.

The printhead 26 may be an integral part of the printing system 12', or it may be user replaceable. When the printhead 26 is user replaceable, it may be removably insertable into a suitable distributor receiver or interface module (not shown).

In another example of the printing system 12', a single inkjet printhead may be used to selectively deliver different coalescent dispersions 28. For example, a first set of printhead nozzles of the printhead may be configured to deliver one of the coalescent dispersions 28, and a second set of printhead nozzles of the printhead may be configured to deliver the other of the coalescent dispersions 28.

As shown in FIG. 4, the distributor 26 has a length that enables it to span the whole width of the support member 58 in a page-wide array configuration. In an example, the page-wide array configuration is achieved through a suitable arrangement of multiple printheads. In another example, the page-wide array configuration is achieved through a single printhead with an array of nozzles having a length to enable them to span the width of the support member 58. In other examples of the printing system 12', the distributor 26 may have a shorter length that does not enable them to span the whole width of the support member 58.

While not shown in FIG. 4, it is to be understood that the distributor 26 may be mounted on a moveable carriage to enable it to move bi-directionally across the length of the support member 58 along the illustrated y-axis. This enables selective delivery of the coalescent dispersion 28 across the whole width and length of the support member 58 in a single pass. In other examples, the distributor 26 may be fixed while the support member 58 is configured to move relative thereto.

As used herein, the term 'width' generally denotes the shortest dimension in the plane parallel to the X and Y axes shown in FIG. 4, and the term 'length' denotes the longest dimension in this plane. However, it is to be understood that in other examples the term 'width' may be interchangeable with the term 'length'. As an example, the distributor 26 may have a length that enables it to span the whole length of the support member 58 while the moveable carriage may move bi-directionally across the width of the support member 58.

In examples in which the distributor 26 has a shorter length that does not enable them to span the whole width of the support member 58, the distributor 26 may also be movable bi-directionally across the width of the support member 58 in the illustrated X axis. This configuration enables selective delivery of the coalescent dispersion 28 across the whole width and length of the support member 58 using multiple passes.

The distributor 26 may include therein a supply of the coalescent dispersion 28, or may be operatively connected to a separate supply of the coalescent dispersion 28.

As shown in FIG. 4, the printing system 12' also includes a sinterable material distributor 56. This distributor 56 is used to provide the layer (e.g., layer 10) of the sinterable material 16 on the support member 58. Suitable sinterable material distributors 56 may include, for example, a wiper blade, a roller, or combinations thereof.

The sinterable material 16 may be supplied to the sinterable material distributor 56 from a hopper or other suitable delivery system. In the example shown, the sinterable material distributor 56 moves across the length (Y axis) of the support member 58 to deposit a layer of the sinterable material 16. As previously described, a first layer of sinterable material 16 will be deposited on the support member 58, whereas subsequent layers of the sinterable material 16 will be deposited on a previously deposited (and solidified) layer.

It is to be further understood that the support member 58 may also be moveable along the Z axis. In an example, the support member 58 is moved in the Z direction such that as new layers of sinterable material 16 are deposited, a predetermined gap is maintained between the surface of the most recently formed layer and the lower surface of the distributor 26. In other examples, however, the support member 58 may be fixed along the Z axis and the distributor 26 may be movable along the Z axis.

Similar to the system 12, the system 12' also includes the radiation source 30 to apply energy to the deposited layer of sinterable material 16 and the coalescent dispersion 28 to cause the solidification of portion(s) 44 of the sinterable material 16. Any of the previously described radiation sources 30 may be used. In an example, the radiation source 30 is a single energy source that is able to uniformly apply energy to the deposited materials, and in another example, radiation source 30 includes an array of energy sources to uniformly apply energy to the deposited materials.

In the examples disclosed herein, the radiation source 30 is configured to apply energy in a substantially uniform manner to the whole surface of the deposited sinterable material 16. This type of radiation source 30 may be referred to as an unfocused energy source. Exposing the entire layer to energy simultaneously may help increase the speed at which a three-dimensional object may be generated.

While not shown, it is to be understood that the radiation source 30 may be mounted on the moveable carriage or may be in a fixed position.

The central processing unit 46 may control the radiation source 30. The amount of energy applied may be in accordance with delivery control data 52.

The system 12' may also include a pre-heater 60 that is used to pre-heat the deposited sinterable material 16 (as shown and described in reference to FIG. 2B). The use of the pre-heater 60 may help reduce the amount of energy that has to be applied by the radiation source 30.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 50° C. to about 350° C. should be interpreted to include not only the explicitly recited limits of about 50° C. to about 350° C., but also to include individual values, such as 57° C., 95° C., 125° C., 250° C., etc., and sub-ranges, such as from about 70° C. to about 225° C., from about 60° C. to about 170° C., etc. Furthermore, when "about" is utilized to describe a value, this is meant to encompass minor variations (up to +/−10%) from the stated value.

In describing and claiming the examples disclosed herein, the singular forms "a", "an", and "the" include plural referents unless the context clearly dictates otherwise.

While several examples have been described in detail, it will be apparent to those skilled in the art that the disclosed examples may be modified. Therefore, the foregoing description is to be considered non-limiting.

What is claimed is:
1. A 3D printed object, comprising:
   multiple sequentially applied layers forming a three-dimensional shape, each of the multiple sequentially applied layers including:
   a sintered and fused sinterable material; and
   an infrared or near-infrared binding agent binding the sintered and fused sinterable material together, the infrared or near-infrared binding agent being a naphthalocyanine having a polar group attached to each side chain thereof, wherein the naphthalocyanine has the structure:

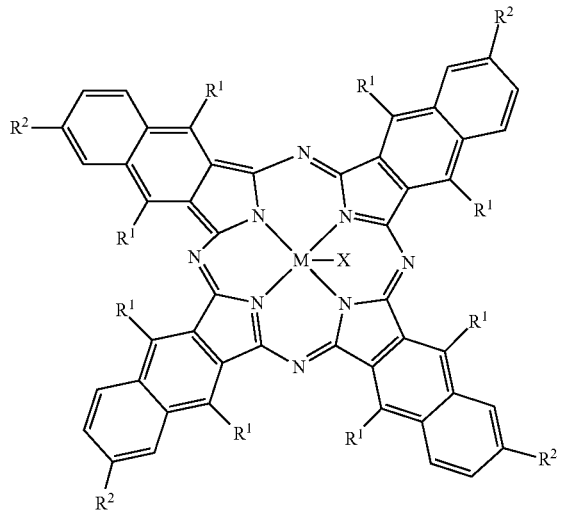

and wherein:
   $R^1$ is H, a $C_1$-$C_{18}$ alkoxy group, or $NH_2$;
   M is selected from the group consisting of Cu, Ti, Zn, Al, Fe, Co, Ga, In, Mn, Y, and Si;
   $R^2$ is selected from the group consisting of a phosphate and an ethylene oxide; and
   X is present when M is more than divalent, and X is selected from the group consisting of a halogen; OH; OCOR, where R is H or a $C_1$-$C_{18}$ alkyl group; COOZ, where Z is Li, Na, or K; $SO_3Z$, where Z is Li, Na, or K; $PO_3Z$, where Z is Li, Na, or K;
   $NR^3_4{}^+$, where $R^3$ is H or a $C_1$-$C_{18}$ alkyl group; and $O(CH_2CH_2O)_mCH_3$, where m=1 to 500.

2. The 3D printed object as defined in claim 1, further comprising a gloss enhancing agent.

3. The 3D printed object as defined in claim 1 wherein M is selected from the group consisting of In and Y.

4. A three-dimensional (3D) printing method, comprising:
   selecting a coalescent dispersion for forming the 3D printed object of claim 1, the coalescent dispersion including:
      an aqueous vehicle; and
      the infrared or near-infrared binding agent dissolved or dispersed in the aqueous vehicle;
   depositing a sinterable material;
   heating the sinterable material to a temperature ranging from about 50° C. to about 350° C.;
   selectively applying the coalescent dispersion on at least a portion of the sinterable material; and
   exposing the sinterable material and the coalescent dispersion applied thereon to infrared or near-infrared radiation, whereby the infrared or near-infrared binding agent absorbs the radiation and converts the absorbed radiation to thermal energy, thereby at least curing the at least the portion of the sinterable material in contact with the infrared or near-infrared binding agent and forming a first layer of the three-dimensional object.

5. The 3D printing method as defined in claim 4 wherein the coalescent dispersion includes:
   the infrared or near-infrared binding agent present in an amount ranging from about 0.1 wt % to about 50 wt % with respect to a total weight of the coalescent dispersion;

a surfactant present in an amount ranging from about 0.5 wt % to about 40 wt % with respect to the total weight of the coalescent dispersion;

a co-solvent present in an amount ranging from about 1 wt % to about 40 wt % with respect to the total weight of the coalescent dispersion;

a biocide present in an amount ranging from 0.1 wt % to about 1 wt % with respect to the total weight of the coalescent dispersion; and a balance of water.

6. The 3D printing method as defined in claim 4, further comprising:

depositing a second layer of the sinterable material on the first layer of the three-dimensional object;

heating the second layer of the sinterable material to a temperature ranging from about 50° C. to about 350° C.;

selectively applying a second layer of the coalescent dispersion on at least a portion of the second layer of the sinterable material; and exposing the second layer of the sinterable material and the second layer of the coalescent dispersion to infrared or near-infrared radiation, whereby the infrared or near-infrared binding agent in the second layer of the coalescent dispersion absorbs the radiation and converts the absorbed radiation to thermal energy, thereby at least curing the at least the portion of the second layer of the sinterable material in contact with the infrared or near-infrared binding agent of the second layer of the coalescent dispersion and forming a second layer of the three-dimensional object.

7. The 3D printing method as defined in claim 6, further comprising repeating the depositing, heating, selectively applying, and exposing to create subsequent layers of the three-dimensional object.

8. The 3D printing method as defined in claim 7, further comprising exposing the three-dimensional object to a water treatment, thereby removing any unbound infrared or near-infrared binding agent.

9. The 3D printing method as defined in claim 8, further comprising:

incorporating the unbound infrared or near-infrared binding agent into an other coalescent dispersion; and utilizing the other coalescent dispersion to form an other three-dimensional object.

10. A 3D printed object, comprising:

multiple sequentially applied layers forming a three-dimensional shape, each of the multiple sequentially applied layers including:

a sintered and fused sinterable material; and an infrared or near-infrared binding agent binding the sintered and fused sinterable material together, the infrared or near-infrared binding agent being a phthalocyanine having a polar group attached to each side chain thereof, wherein the phthalocyanine has the structure:

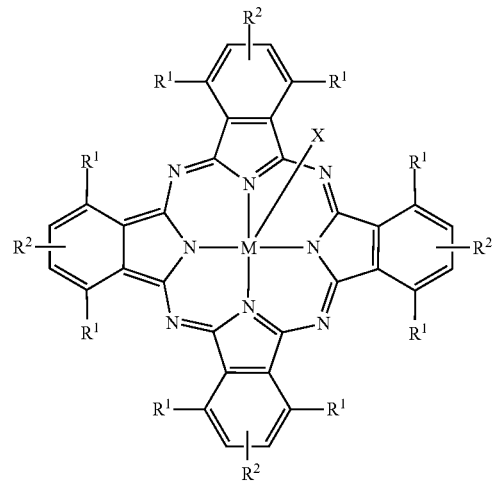

wherein:
$R^1$ is H, a $C_1$-$C_{18}$ alkoxy group, or $NH_2$;
M is selected from the group consisting of In, Tl, Y, and Sc;
$R^2$ is selected from the group consisting of a sulfonate, a phosphate, and an ethylene oxide; and
X is present when M is more than divalent, and X is selected from the group consisting of a halogen; OH; OCOR, where R is H or a $C_1$-$C_{18}$ alkyl group; COOZ, where Z is Li, Na, or K; $SO_3Z$, where Z is Li, Na, or K; $PO_3Z$, where Z is Li, Na, or K; $NR^3_4{}^+$, where $R^3$ is H or a $C_1$-$C_{18}$ alkyl group; and $O(CH_2CH_2O)_mCH_3$, where m 32 1 to 500.

11. The 3D printed object as defined in claim 10, further comprising a gloss enhancing agent.

12. The 3D printed object as defined in claim 10 wherein $R^2$ is selected from the group consisting of a phosphate and an ethylene oxide.

13. A three-dimensional (3D) printing method, comprising:

selecting a coalescent dispersion for forming the 3D printed object of claim 10, the coalescent dispersion including:

an aqueous vehicle; and the infrared or near-infrared binding agent dissolved or dispersed in the aqueous vehicle;

depositing a sinterable material;

heating the sinterable material to a temperature ranging from about 50° C. to about 350° C.;

selectively applying the coalescent dispersion on at least a portion of the sinterable material; and exposing the sinterable material and the coalescent dispersion applied thereon to infrared or near-infrared radiation, whereby the infrared or near-infrared binding agent absorbs the radiation and converts the absorbed radiation to thermal energy, thereby at least curing the at least the portion of the sinterable material in contact with the infrared or near-infrared binding agent and forming a first layer of the three-dimensional object.

14. The 3D printing method as defined in claim 13 wherein the coalescent dispersion includes:

the infrared or near-infrared binding agent present in an amount ranging from about 0.1 wt % to about 50 wt % with respect to a total weight of the coalescent dispersion;

a surfactant present in an amount ranging from about 0.5 wt % to about 40 wt % with respect to the total weight of the coalescent dispersion;

a co-solvent present in an amount ranging from about 1 wt % to about 40 wt % with respect to the total weight of the coalescent dispersion;

a biocide present in an amount ranging from 0.1 wt % to about 1 wt % with respect to the total weight of the coalescent dispersion; and a balance of water.

15. The 3D printing method as defined in claim 14 wherein the coalescent dispersion further includes a gloss enhancing agent in an amount ranging from about 1 wt % to about 25 wt % with respect to the total weight of the coalescent dispersion.

16. The 3D printing method as defined in claim 15, further comprising enhancing gloss of the first layer of the three-dimensional object by increasing a voxel density of the coalescent dispersion at a perimeter of the selectively applied coalescent dispersion.

17. The 3D printing method as defined in claim 14, further comprising imparting color to an interior and an exterior of the first layer of the three-dimensional object by incorporating a pigment into the coalescent dispersion, wherein the pigment is present in an amount ranging from about 1 wt % to about 10 wt % with respect to the total weight of the coalescent dispersion.

18. The 3D printing method as defined in claim 14 wherein:

the coalescent dispersion is colorless; and the method further comprises imparting color to an exterior of the first layer of the three-dimensional object by selectively applying, at a perimeter of the selectively applied colorless coalescent dispersion, a colored coalescent dispersion including:

an infrared or near-infrared binding agent present in an amount ranging from about 0.1 wt % to about 50 wt % with respect to a total weight of the colored coalescent dispersion;

a pigment present in an amount ranging from about 1 wt % to about 10 wt % with respect to the total weight of the colored coalescent dispersion;

a surfactant present in an amount ranging from about 0.5 wt % to about 40 wt % with respect to the total weight of the colored coalescent dispersion;

a co-solvent present in an amount ranging from about 1 wt % to about 40 wt % with respect to the total weight of the colored coalescent dispersion;

a biocide present in an amount ranging from 0.1 wt % to about 1 wt % with respect to the total weight of the colored coalescent dispersion; and a balance of water.

* * * * *